US007583172B2

(12) United States Patent
Koonce

(10) Patent No.: US 7,583,172 B2
(45) Date of Patent: Sep. 1, 2009

(54) MULTI-FREQUENCY ELECTROMAGNETIC FIELD GENERATOR

(76) Inventor: Gene Koonce, 2329 10th St., Greeley, CO (US) 80634

( * ) Notice: Subject to any disclaimer, the term of this patent is extended or adjusted under 35 U.S.C. 154(b) by 0 days.

(21) Appl. No.: 12/131,733

(22) Filed: Jun. 2, 2008

(65) Prior Publication Data

US 2008/0297293 A1 Dec. 4, 2008

Related U.S. Application Data

(60) Provisional application No. 60/941,601, filed on Jun. 1, 2007.

(51) Int. Cl.
*A61N 5/00* (2006.01)

(52) U.S. Cl. ......................... 335/296; 335/299; 606/33; 607/1; 607/88; 361/230; 361/232; 313/153; 313/154; 313/155

(58) Field of Classification Search ................. 335/296, 335/299; 606/32, 33; 607/1, 88, 90, 100–103; 361/230, 232; 313/153–155
See application file for complete search history.

(56) References Cited

U.S. PATENT DOCUMENTS 5,908,444 A 6/1999 Azure
6,217,604 B1 4/2001 Azure et al.
6,933,819 B1 8/2005 Koonce

*Primary Examiner*—Ramon M Barrera
(74) *Attorney, Agent, or Firm*—William W. Cochran; Cochran Freund & Young LLC

(57) ABSTRACT

Disclosed is a multi-frequency electromagnetic field generator that is capable of generating electromagnetic flux fields that are projected at a distance from the device. Radial fields, horizontal fields and spiral fields are generated by the electromagnetic field generator and are projected at a distance from the device. A wide range of frequencies is generated as a result of the fast rise time pulses produced by the device. The geometry and structure of the device cause the electromagnetic fields to encircle the device and be collected at the far end of the device by an antenna. An inner coil antenna, that is centrally disposed in the device, receives electromagnetic waves that are transformed into a current that is applied to an inner coil. The inner coil produces a strong electromagnetic field that extends outwardly in a horizontal direction that increases the projected horizontal distance of the electromagnetic field.

4 Claims, 8 Drawing Sheets

MULTI-FREQUENCY ELECTROMAGNETIC FIELD GENERATOR

CROSS-REFERENCE TO RELATED APPLICATION

This application claims benefit of and priority to U.S. Provisional Patent Application Ser. No. 60/941,601, entitled "Improved Multi-Frequency Electromagnetic Field Generator" by Gene Koonce, filed Jun. 1, 2007, the entire contents of which are specifically incorporated herein by reference for all that it discloses and teaches.

BACKGROUND OF THE INVENTION

Various types of electromagnetic field generators have existed for some time. For example, U.S. Pat. No. 6,933,819 describes an electromagnetic field generator that is capable of generating multiple frequencies. This patent is specifically incorporated herein, by reference, for all that it discloses and teaches. Multi-frequency electromagnetic generators can be used for various purposes, including use as energy transfer devices. Electromagnetic field generators can also be used for testing and calibration of flux meters, including flux meters capable of detecting multiple frequencies.

SUMMARY OF THE INVENTION

An embodiment of the present invention may therefore comprise an electromagnetic field generator that is capable of generating spiral, radial and horizontal electromagnetic fields comprising: a spiral transmission coil that is horizontally disposed in the container that creates a multi-frequency spiral electromagnetic field in response to a high voltage pulse created by the electrical components; a column disposed on the container; a Tesla coil wound around the column having a first end connected to electrical ground; emission tubes mounted on the column having first electrodes that are connected to a second end of the Tesla coil; a first antenna mounted over the emission tubes that is electrically connected to second electrodes of the emission tubes, the antenna disposed to couple to multi-frequency spiral electromagnetic field such that a current is induced in the antenna and flows through the antenna to generate a horizontally disposed electromagnetic field, the current also flowing through the emission tubes to create light wave frequency electromagnetic radiation and through the Tesla coil to generate a centrally disposed electromagnetic field; a second antenna mounted substantially centrally between the emission tubes that is disposed to couple to the centrally disposed electromagnetic field that induces a current in a conductor attached to the second antenna; an inner coil antenna, that is connected to the conductor, the inner coil antenna generating an additional horizontally disposed electromagnetic field.

An embodiment of the present invention may further comprise a method of generating multi-frequency electromagnetic fields with an electromagnetic generator comprising: providing a horizontally disposed flat spiral transmitting coil that creates a multi-frequency spiral electromagnetic field; placing a Tesla coil that is centrally located over the spiral transmitting coil, the Tesla coil having a center axis that is substantially normal to the flat spiral coil; mounting emission tubes in alignment with the Tesla coil; mounting a first antenna over the emission tubes that is disposed to receive the multi-frequency spiral electromagnetic field such that a current is induced in the first antenna which generates a horizontally disposed electromagnetic field, the current also flowing through the emission tubes to create electromagnetic radiation and through the Tesla coil to generate a centrally disposed electromagnetic field; mounting a second antenna that is centrally disposed between the emission tubes to receive the centrally disposed electromagnetic field; providing an inner coil antenna, that is connected to the second antenna with a conductor, the inner coil antenna generating an additional horizontally disposed electromagnetic field from current induced in the second antenna from the centrally disposed electromagnetic field.

DETAILED DESCRIPTION OF THE INVENTION

Figure 1:
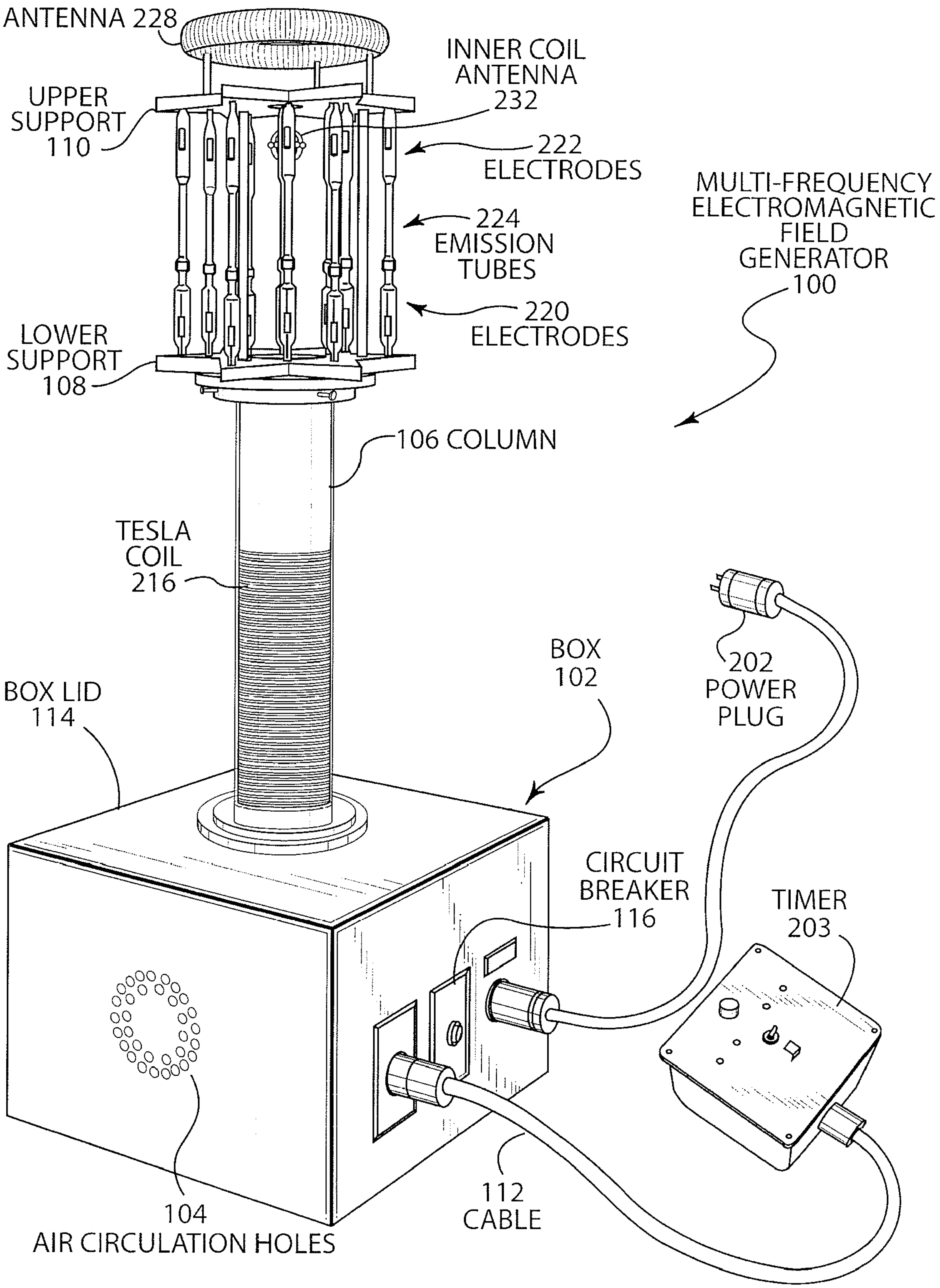
FIG. 1 is as illustration of one embodiment of an electromagnetic generator.
Figure 2:
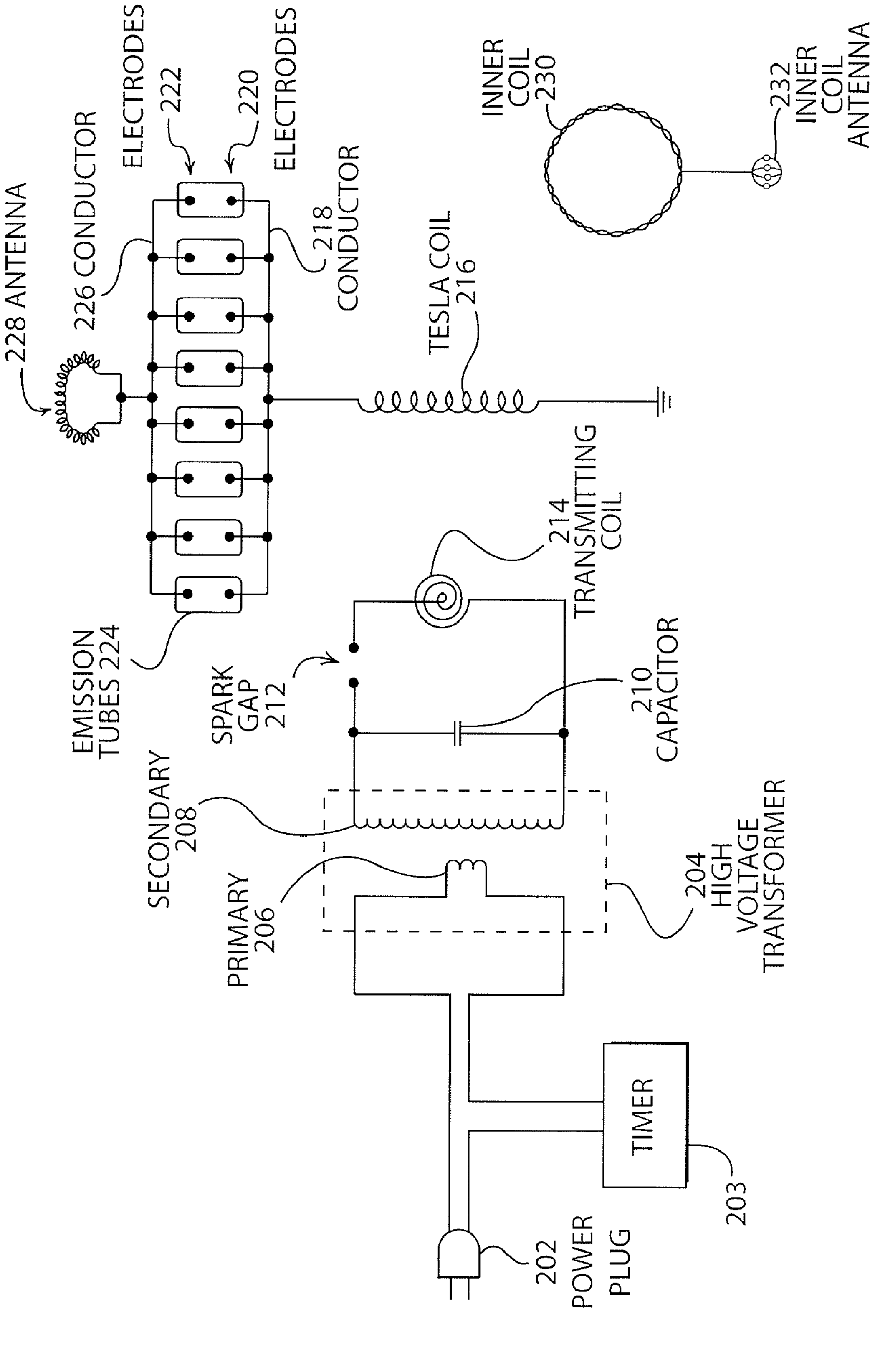
FIG. 2 is a schematic circuit diagram of the embodiment of FIG. 1.
Figure 7:
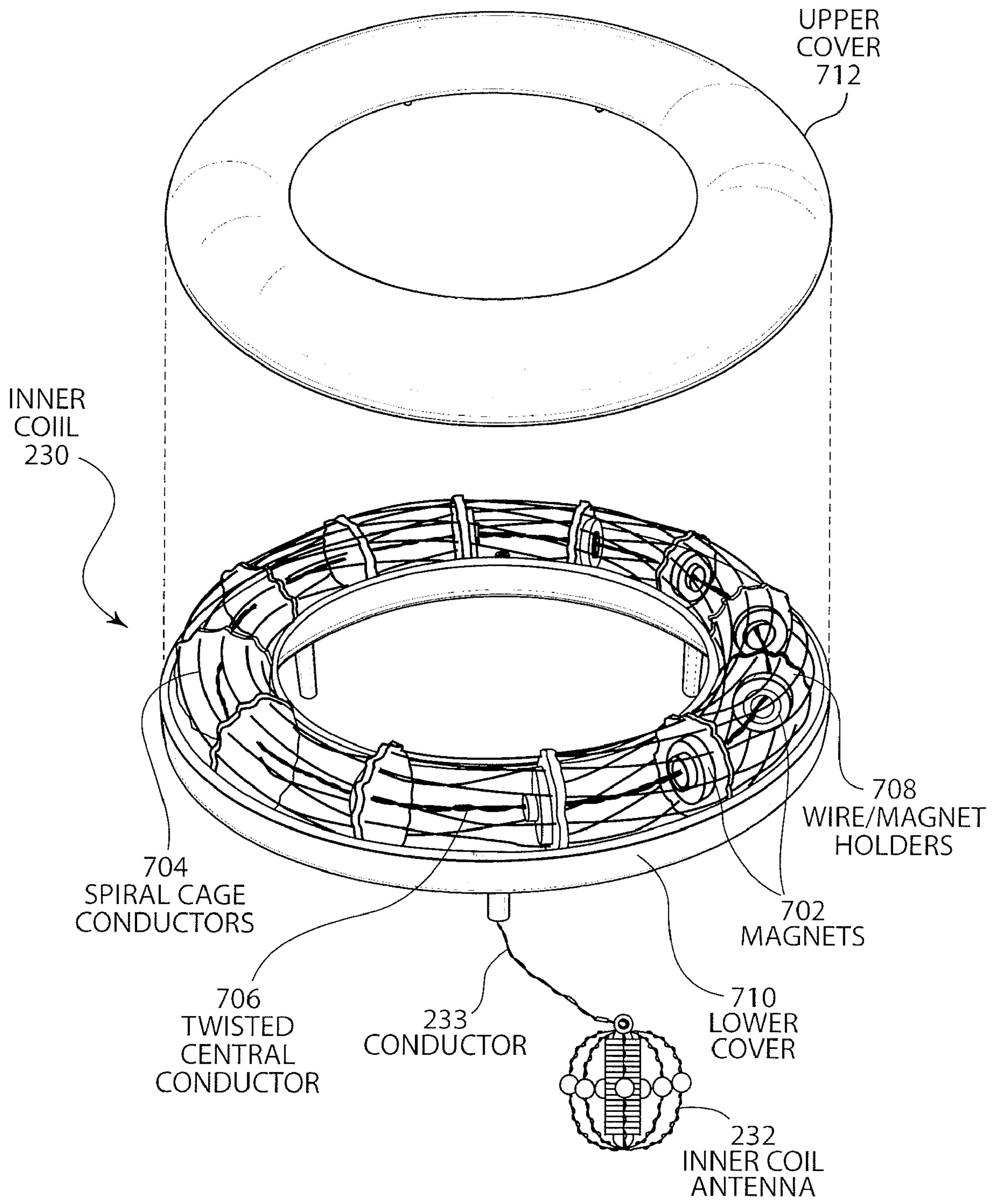
FIG. 7 is an illustration of one embodiment of an inner coil and inner coil antenna.

FIG. 1 is an isometric view of one embodiment of a multi-frequency electromagnetic field generator 100. As shown in FIG. 1, box 102 contains various electronics. Box 102 may be made from a material such as Bakelite or Phenolic and can take any shape. This material substantially restricts the emanation of electric fields that are generated by the electrical devices contained within box 102. Of course, any type of materials can be used to shield the electric field radiation including foils, screens, faraday cages, etc. Air circulation holes 104 provide air circulation to the interior of the box where the electronics are located. Fans may be provided to increase the airflow, which may be located within the box 102. Mounted on the top of the box 102 is a column 106. The column 106 is attached to a lower support 108. Disposed between the lower support 108 and upper support 110 are a series of emission tubes 224. Each of the emission tubes 224 has electrodes 220 located on the bottom portion of the tube and electrodes 222 located on the top portions of the tube. As indicated in FIG. 2, the bottom electrodes 220 are connected to the Tesla coil 216, while the top electrodes 222 are connected to the antenna 228. Tesla coil 216 is wrapped around the column 106. The top of the Tesla coil 216 is electrically connected to the electrodes 220, as mentioned above. The bottom of the Tesla coil 216 is a wire that projects through a hole in the box lid 114 and is connected to electrical ground. The antenna 228 is mounted on top of the upper support 110 and functions to collect electromagnetic flux signals that project from the box 102. The electronics within the box are connected to a power source through power plug 202. The circuit breaker 116 is provided to protect the device from over-voltage or over-current conditions. The timer 203 is connected via cable 112 to the device and intermittently interrupts the power signal from power plug 202 to allow the electrical components within the box 102 to adequately cool. The inner coil antenna 232 is centrally located between the emission tubes 224 and is coupled to the magnetic flux from the Tesla coil 216 and spiral coil 214 (FIG. 2) that travels through the column 106 and through the central portion between the emission tubes 224. The inner coil antenna 232 is connected by an electrical connector to an inner coil 230 that is located inside the antenna 228 (FIG. 7).

Figure 3:
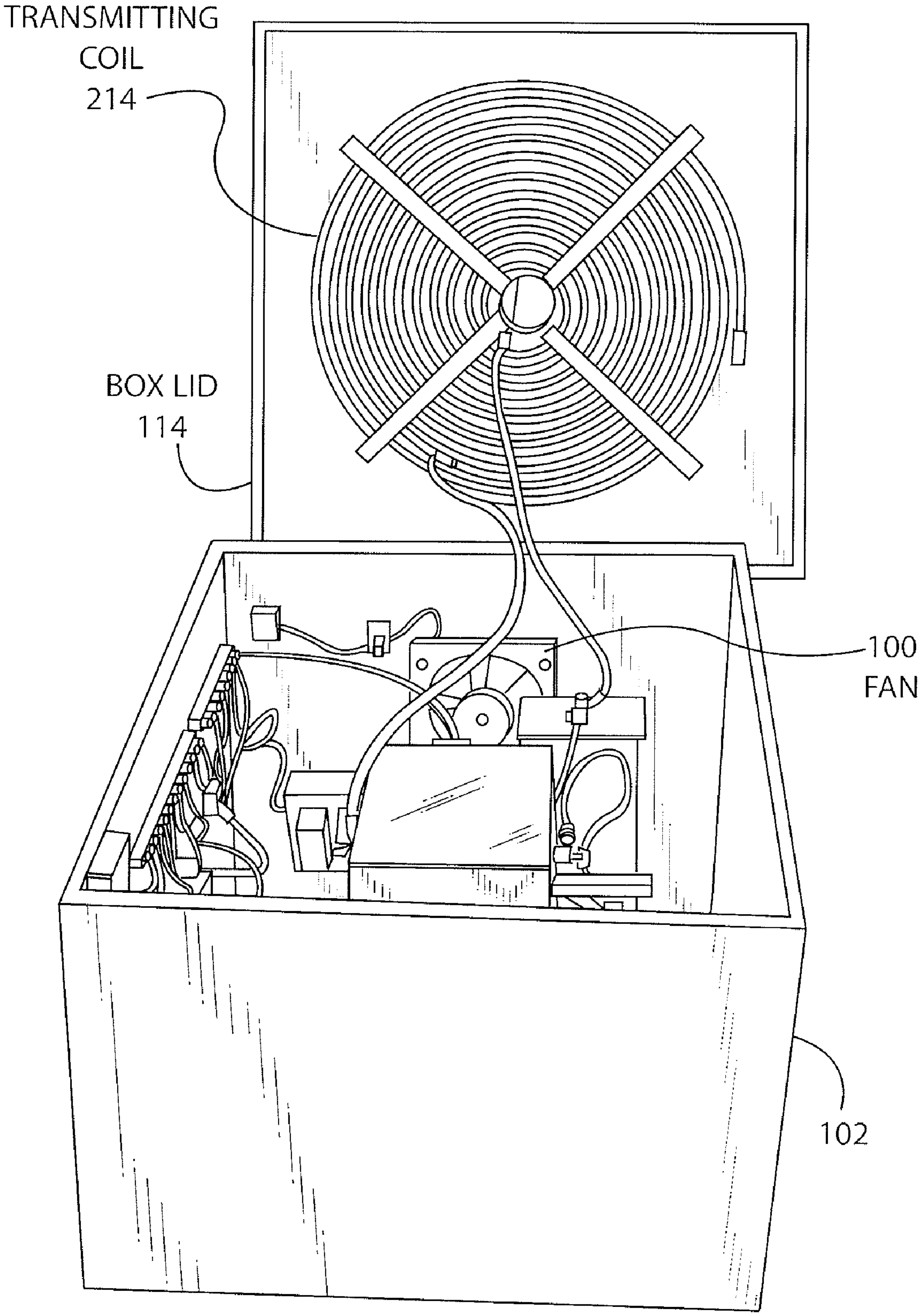
FIG. 3 is an illustration of the contents of the box of the device illustrated in FIG. 1.
Figure 5:
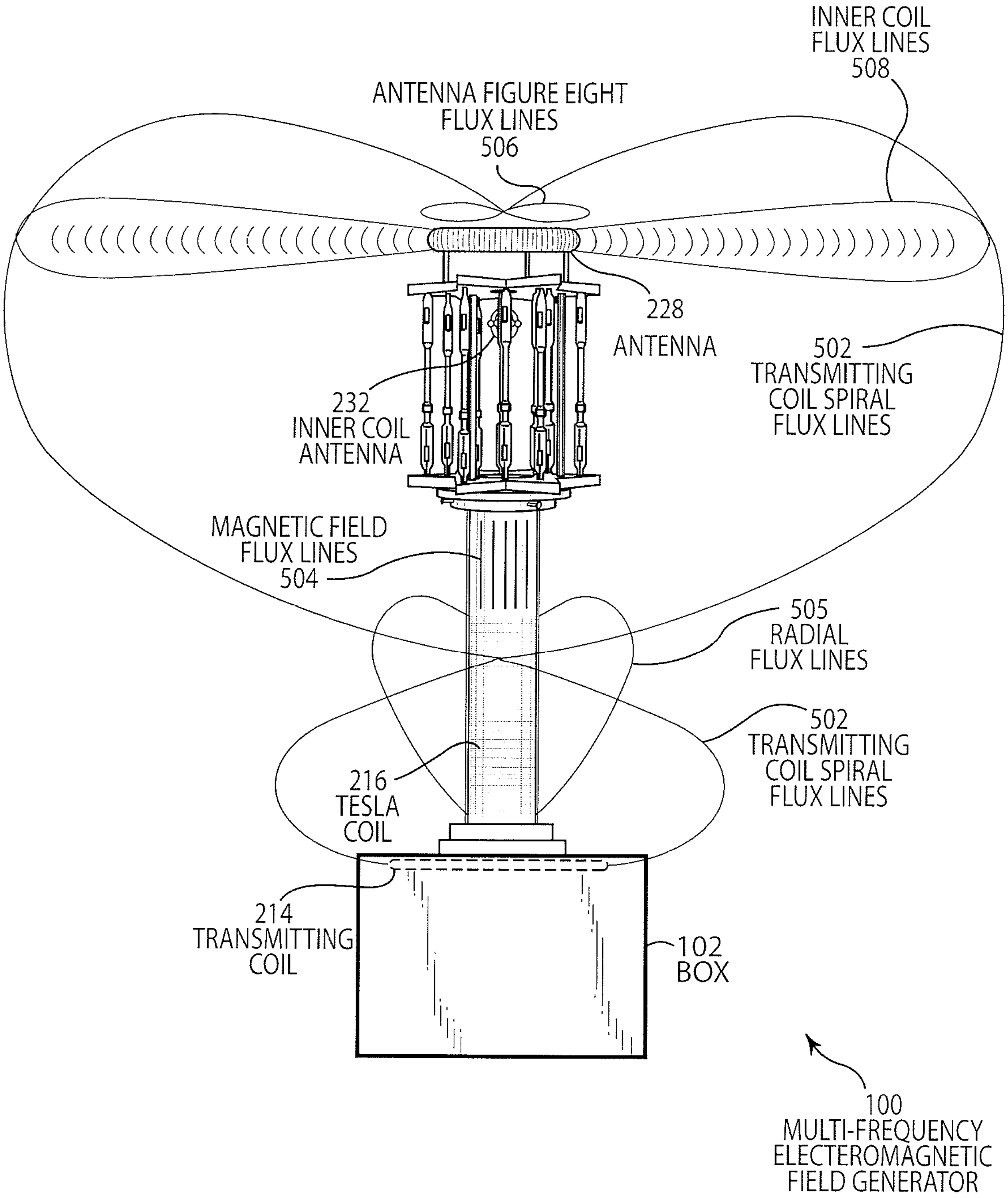
FIG. 5 is a side view illustrating the flux lines created by the device of FIG. 1.

FIG. 2 is a schematic circuit diagram of the embodiment illustrated in FIG. 1. As shown in FIG. 2, power plug 202 is connected to a timer 203 that periodically interrupts the flow of power to the high voltage transformer 204. The higher voltage transformer 204 comprises a primary winding 206 and a secondary winding 208. The 117 volt RMS AC voltage is transformed by the high voltage transformer 204 to create an RMS voltage of approximately 6,000 volts on the secondary 208. Connected across the secondary 208 is a large capacitor 210 that charges both positively and negatively in response to the 6,000 volt sine wave that is applied to the secondary 208. Spark gap 212 is adjusted so that a discharge occurs at a voltage level below 6,000 volts. This causes the capacitor 210 to discharge and to recharge on the next leg of the sine wave. The spark gap effectively creates a short circuit which discharges the capacitor very quickly and causes a sharp pulse to be generated in the transmitting coil 214. The rise time of the pulse results in a wide frequency spectrum of electromagnetic energy that emanates from the transmitting coil 214. A Fourier transform of the short rise time pulse created by the discharge of the capacitor through the spark gap illustrates the large multitude of harmonic waveforms that are generated by such a steep pulse. In this fashion, multiple frequencies are created by the multi-frequency electromagnetic generator. Transmitting coil 214 is a spiral coil that is mounted on the inside box lid 114, as illustrated in FIG. 3. The transmitting coil 214 generates a large electromagnetic pulse that creates spiral flux lines 502, as illustrated in FIG. 5. Because of the spiral shape of the transmitting coil 214, spirally shaped electromagnetic fields emanate from the box 102 of FIG. 1 that are coupled to the antenna 228, as explained in more detail below.

As illustrated in FIG. 5, the spiral flux lines are coupled to the antenna 228. This causes a charge to develop on conductor 226 which is coupled to the electrodes 222 and the emission tubes 224. The transmitting coil 214, illustrated in FIG. 2, also generates a centrally located electromagnetic pulse that is shown as electromagnetic field flux lines 504 (FIG. 5). Flux lines 504 are transmitted through the opening in the box lid 114, through the column 106, and are coupled to inner coil antenna 232 and antenna 228. The electromagnetic field pulse that is represented by flux lines 504 causes additional current to be generated in the antenna 228 and Tesla coil 216 and also generates a current in inner coil antenna 232, as explained below. The emission tubes 224 contain various gases such as hydrogen and noble gases that are excited and transition to create electromagnetic emissions in the visible spectrum, IR spectrum and far IR spectrum or any desired spectrum. The ionization of the gases in the emission tubes 224 causes the electrical current to flow to electrodes 220 and conductor 218. Conductor 218 is connected to one end of Tesla coil 216. The other end of Tesla coil 216 is coupled to ground. Hence, the electrical current from the electromagnetic waves emitted by transmitting coil 214 causes a current to flow through the Tesla coil 216 to ground. The electromagnetic field generated by the Tesla coil 216 supplements and forms a part of the strong electromagnetic field 504. Electromagnetic field 504 flows vertically through the opening in the column 106 and the center part of the area between the emission tubes 224. The electromagnetic field 504 is received by the inner coil antenna 232, that is electrically connected to the inner coil 230, that generates the inner coil 230 strong electromagnetic field 508 (FIG. 5).

FIG. 3 is an illustration of the electrical components in the box 102. The spiral transmitting coil 214 is mounted on the box lid 114. The spiral transmitting coil 214 is centered on the opening in the box lid 114. When the box lid 114 is in place on the box 102, the transmitting coil is located in a horizontal position which causes the emission of electromagnetic waves horizontally from the underside of the box lid 114. Fan 100 is also shown in box 102 that ensures air circulation through the interior of box 102.

Figure 4:
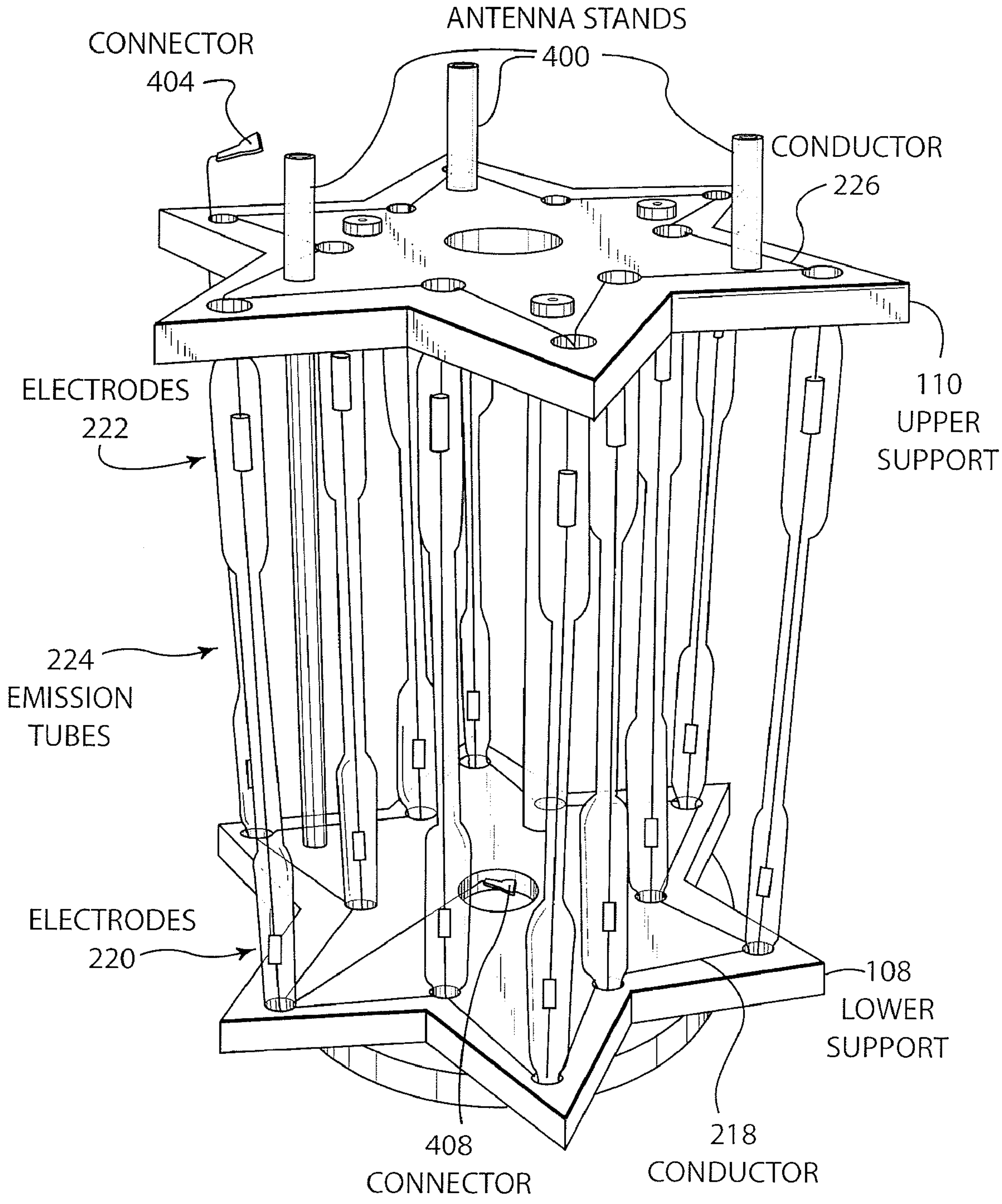
FIG. 4 is a schematic illustration of the emission tubes and supporting structure of the device of FIG. 1.

FIG. 4 is an illustration of the emission tubes structure. As shown in FIG. 4, the emission tubes 224 are supported by a lower support 108 and an upper support 110. Conductor 226 is disposed on the upper support 110 and connects each of the electrodes 222 together. Conductor 226 is connected to a connector 404, which in turn connects to the antenna 228. Antenna 228 is mounted on antenna stands 400. Similarly, conductor 218 connects each of the electrodes 220 together. Connector 408 is connected to conductor 218. Connector 408 connects the conductor 218 to the top of the Tesla coil 216.

FIG. 5 is a side view of an embodiment of a multi-frequency electromagnetic field generator that is illustrated in FIG. 1 showing various flux lines generated by the device. As shown in FIG. 5, box 102 has a transmitting coil 214 mounted on the underside of the lid of the box 102. Transmitting coils 214 emit spiral flux lines 502 that emanate from the side of the box 102 and spiral around the device to connect into the antenna 228. The horizontal disposition of the transmitting coil 214 causes the flux lines 502 to emanate in a radial direction from box 102. Since the antenna 228 is mounted at the opposite end of the electromagnetic field generator, large flux line fields are created which expand the area of influence of the electromagnetic fields created by the electromagnetic field generator. Antenna 228 creates a series of figure eight flux lines 506 as a result of the induced current from the flux lines 502. Flux lines 504 are created by transmitting coil 514 and are reinforced by the electromagnetic field of Tesla coil 216. Flux lines 506, generated by the antenna 228, emanate horizontally from the electromagnetic field generator. Electromagnetic field flux lines 504 flow through the central portion of the Tesla coil 216, the column 106, the central portion of the emission tubes 224, and are at least partially coupled to the inner coil antenna 232, that is centrally located between the emission tubes 224. As disclosed in FIG. 2, the inner coil antenna 232 is electrically connected to an inner coil 230 that creates the horizontally disposed inner coil electromagnetic field flux lines 508. The inner coil antenna 232 and the inner coil 230 are able to couple to the electromagnetic field 504, so as to generate the inner coil electromagnetic field flux lines 508 that emanate in a horizontal direction outwardly away from the device, as illustrated in FIG. 5. Since the flux lines 508 emanate in a projected fashion away from the electromagnetic generator, users of the electromagnetic generator can be easily coupled to the electromagnetic field flux lines.

Figure 6:
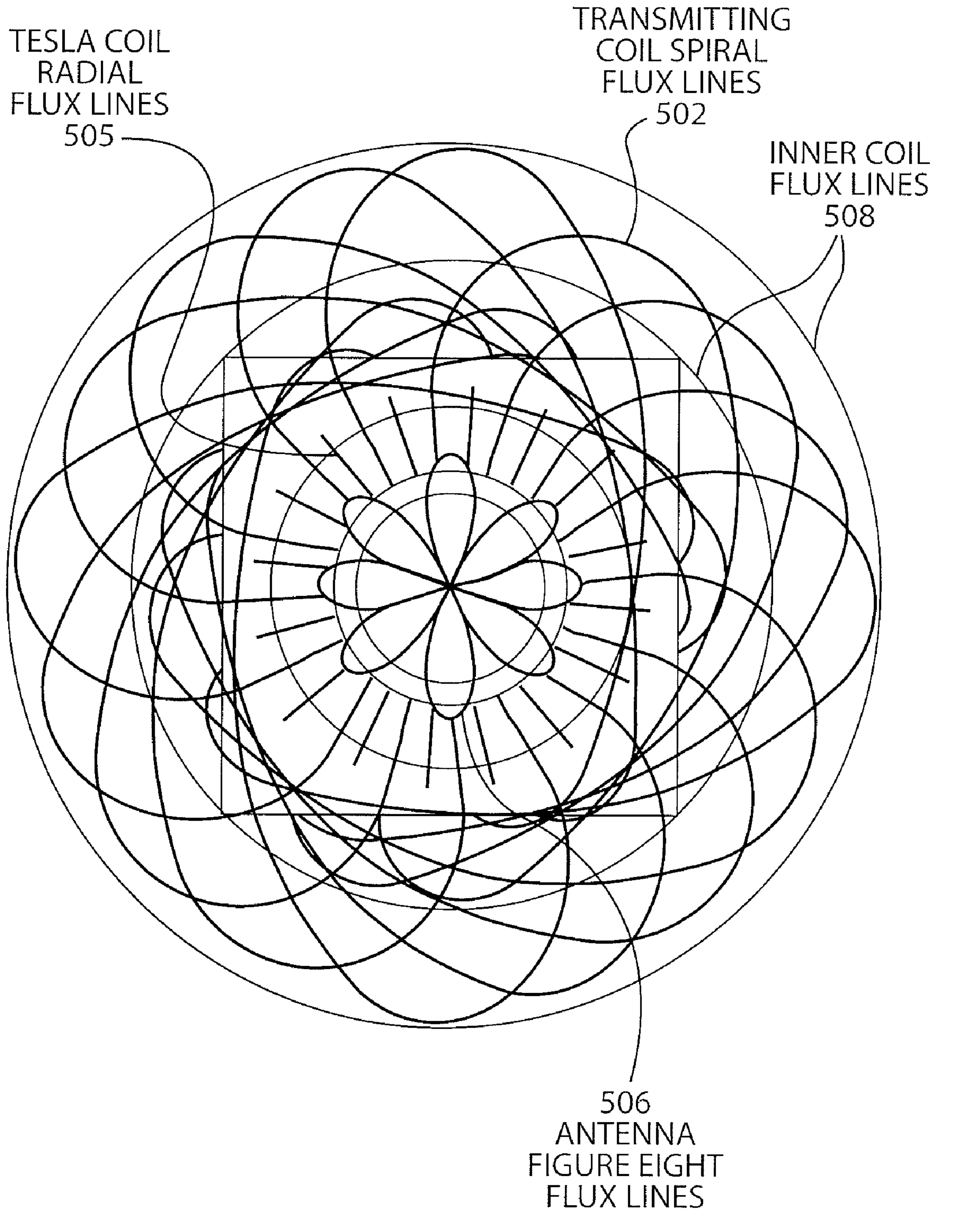
FIG. 6 is a top view illustrating the flux lines created by the device of FIG. 1.

FIG. 6 is a schematic top view of the various flux lines generated by the electromagnetic field generator. As shown in FIG. 6, transmitting coil spiral flux lines 502 emanate from the box 102 and spiral around the electromagnetic field generator to an opposite side where the flux lines 502 are collected by the antenna 228. As also shown in FIG. 6, the antenna creates antenna figure eight flux lines 506 that emanate in a horizontal direction. Further, the Tesla coil creates Tesla coil flux lines 505 that emanate in a radial direction outwardly from the Tesla coil. The inner coil flux lines 508 are also schematically illustrated in FIG. 6. The inner coil flux lines 508 cause the spiral flux lines 502 to project outwardly in a horizontal direction away from the multi-frequency electromagnetic generator 100. The inner coil flux lines 508 are schematically illustrated as a substantially flat field in FIG. 6.

FIG. 7 is a schematic illustration showing the inner coil 230 and the cover that holds the inner coil 230, which is made up of the upper cover 712 and the lower cover 710. The upper cover 712 and lower cover 710 are made from a Lexan material, which easily transmits electromagnetic flux into and out of the inner coil 230. Any material can be used that allows transmission of the electromagnetic field. The inner coil 230 has a twisted central conductor 706 that is formed of three wires that are twisted together. The ends of each of the three wires are connected, #1 to #2, #2 to #3, and #3 to #1, to provide a continuous twisted coil. The inner coil antenna 232 has a connector 233 that is connected to the twisted central conductor 706 at one of the connection points of the twisted central conductor 706. Each of the wires of the twisted central conductor 706 is approximately 20.64 inches long, but can be any desired length. The twisted central conductor 706 is disposed through openings in the wire/magnet holders 708. Neodymium magnets 702, having a central opening, are mounted on the wire/magnet holders 708 so that the twisted central conductor 706 passes through the central opening in the magnets 702. The magnets 702 can be neodymium magnets, or other types of magnets, as desired. Neodymium magnets are used because of the high strength magnetic field generated by neodymium magnets. The wire/magnet holders 708 have a series of equally spaced notched wire holders on their periphery to hold the spiral cage conductors 704 in an equally spaced manner around the periphery of the wire/magnet holders 708. The wire/magnet holders 708 have twelve spaced wire holding notches to hold twelve spiral cage conductors 704 around the periphery of the wire/magnet holders 708. The spiral cage conductors 704 comprise a single conductor that is connected front to end. In the embodiment illustrated in FIG. 7, there are twelve wire/magnet holders 708 and each of the wire/magnet holders 708 is sequentially advanced one-twelfth of a turn in a serial progression around the inner coil 230. As such, the spiral cage conductors 704 are advanced in a spiral fashion one-twelfth of a turn for each wire/magnet holder 708.

Figure 8:
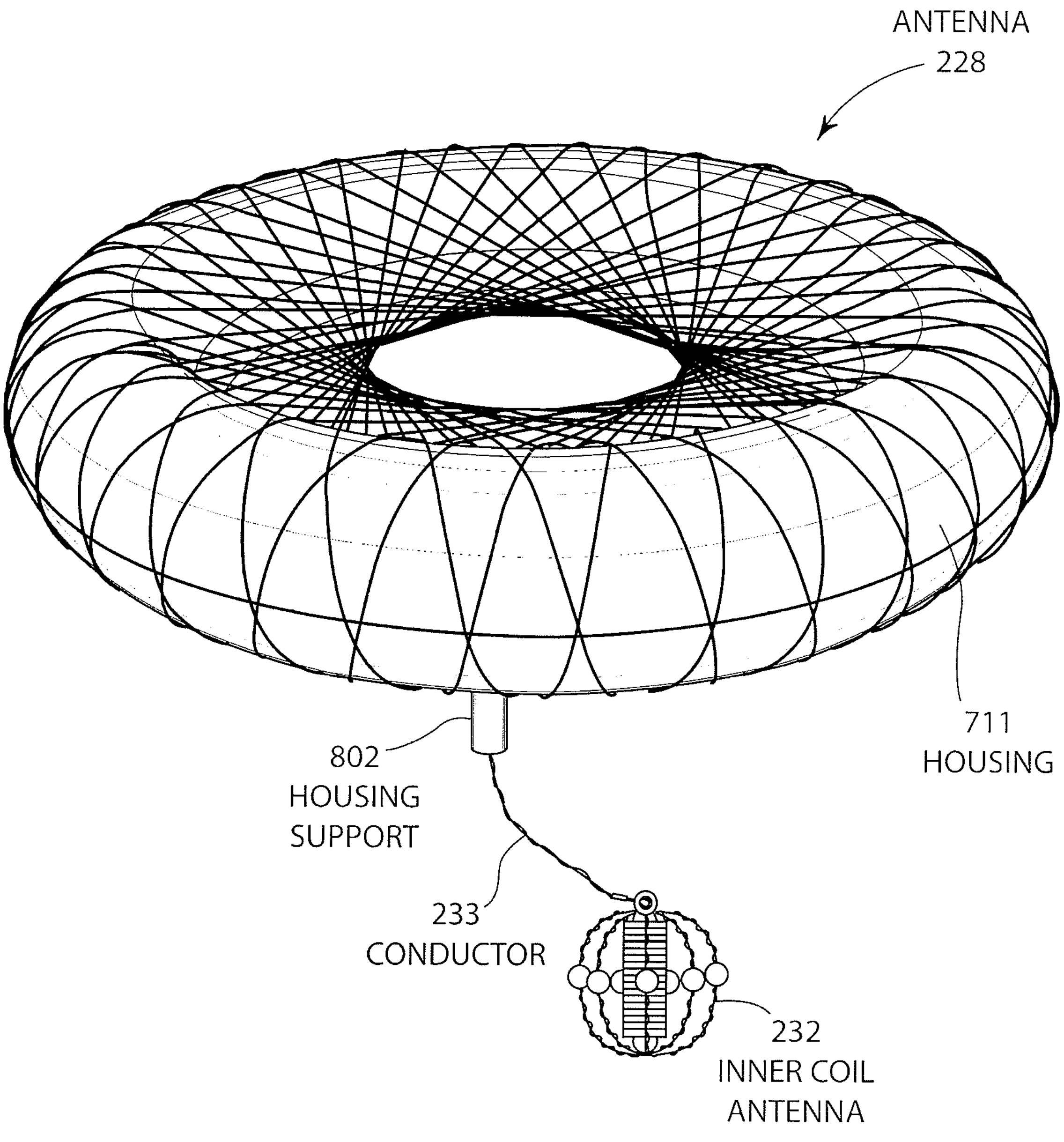
FIG. 8 is an illustration of an antenna that couples electromagnetic fields to a transmitting coil.

FIG. 8 is an illustration of an embodiment illustrating the manner in which the outer antenna 228 is wrapped around the Lexan cover illustrated in FIG. 7. As shown in FIG. 8, the antenna 228 is progressively wrapped around the housing 711 that comprises the upper cover 712 and lower cover 710. As disclosed above, the antenna 228 is connected to the connector 404 illustrated in FIG. 4. The manner in which the antenna 228 is wrapped around the housing 711 provides a central opening in the antenna 228, in which electromagnetic field flux lines 504 from the Tesla coil 216 emanate. The inner coil antenna 232 is centrally disposed under the housing 711 to receive the electromagnetic field 504 and generate a current in conductor 233, which is fed to the inner coil 230. Conductor 233 is disposed through an opening in one of the housing stands 802 to contact the inner coil 230. The current induced in the conductor 233 is transmitted to the inner coil 230, which generates the inner coil electromagnetic flux lines 508 that are illustrated in FIGS. 5 and 6. Of course, all of the flux lines shown in FIGS. 5 and 6 show the manner in which the flux lines emanate from the electromagnetic pulse generator. In other words, the flux lines shown in FIGS. 5 and 6 show the shape of the flux lines and do not show the relative size or strength of the projection of the flux lines from the electromagnetic pulse generator.

The present invention therefore provides a multi-frequency electromagnetic field generator that creates a large number of harmonic electromagnetic waves that project outwardly from the electromagnetic field generator in various ways including radially, horizontally and in a spiral direction. The structure and arrangement of the various components of the electromagnetic field generator creates flux lines that project outwardly in a horizontal direction a substantial distance from the multi-frequency electromagnetic field generator.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An electromagnetic field generator that is capable of generating spiral, radial and horizontal electromagnetic fields comprising:

a spiral transmission coil that is horizontally disposed in a container that creates a multi-frequency spiral electromagnetic field in response to a high voltage pulse created by electrical components;

a column disposed on said container;

a Tesla coil wound around said column having a first end connected to electrical ground;

emission tubes mounted on said column having first electrodes that are connected to a second end of said Tesla coil;

a first antenna mounted over said emission tubes that is electrically connected to second electrodes of said emission tubes, said antenna disposed to couple to said multi-frequency spiral electromagnetic field such that a current is induced in said antenna and flows through said antenna to generate a horizontally disposed electromagnetic field, said current also flowing through said emission tubes to create light wave frequency electromagnetic radiation and through said Tesla coil to generate a centrally disposed electromagnetic field;

an inner coil antenna mounted substantially centrally between said emission tubes that is disposed to couple to said centrally disposed electromagnetic field that induces a current in a conductor attached to said inner coil antenna;

an inner coil that is connected to said conductor, said inner coil generating an additional horizontally disposed electromagnetic field.

2. The electromagnetic field generator of claim 1 wherein said inner coil comprises:

a twisted central conductor;

magnets having a central opening, said twisted central conductor disposed in said magnets;

spiral cage conductors surrounding said twisted central conductor and said magnets.

3. A method of generating multi-frequency electromagnetic fields with an electromagnetic generator comprising:

providing a horizontally disposed flat spiral transmitting coil that creates a multi-frequency spiral electromagnetic field;

placing a Tesla coil that is centrally located over said spiral transmitting coil, said Tesla coil having a center axis that is substantially normal to said flat spiral coil;

mounting emission tubes in alignment with said Tesla coil;

mounting a first antenna over said emission tubes that is disposed to receive said multi-frequency spiral electromagnetic field such that a current is induced in said first antenna which generates a horizontally disposed electromagnetic field, said current also flowing through said emission tubes to create electromagnetic radiation and through said Tesla coil to generate a centrally disposed electromagnetic field;

mounting an inner coil antenna that is centrally disposed between said emission tubes to receive said centrally disposed electromagnetic field;

providing an inner coil, that is connected to said inner coil antenna with a conductor, said inner coil generating an additional horizontally disposed electromagnetic field from current induced in said inner coil antenna from said centrally disposed electromagnetic field.

4. The method of claim 3 wherein said step of providing an inner coil further comprises:

providing an inner coil having a twisted central conductor, magnets having a central opening, said twisted central conductor disposed in said magnets, and spiral cage conductors surrounding said twisted central conductor and said magnets.

* * * * *